United States Patent
Taylor et al.

(10) Patent No.: US 8,932,063 B2
(45) Date of Patent: Jan. 13, 2015

(54) BPH LASER ABLATION SIMULATION

(75) Inventors: Christopher J. Taylor, Arden Hills, MN (US); Jesse R. Haakenson, St. Paul, MN (US)

(73) Assignee: AMS Research Corporation, Minnetonka, MN (US)

(*) Notice: Subject to any disclaimer, the term of this patent is extended or adjusted under 35 U.S.C. 154(b) by 120 days.

(21) Appl. No.: 13/446,551

(22) Filed: Apr. 13, 2012

(65) Prior Publication Data

US 2012/0264096 A1    Oct. 18, 2012

Related U.S. Application Data

(60) Provisional application No. 61/475,870, filed on Apr. 15, 2011.

(51) Int. Cl.

| | | |
|---|---|---|
| *G09B 23/28* | (2006.01) | |
| *A61B 19/00* | (2006.01) | |
| *A61B 18/00* | (2006.01) | |
| *G09B 23/30* | (2006.01) | |
| *A61B 17/00* | (2006.01) | |

(52) U.S. Cl.
CPC .......... *G09B 23/28* (2013.01); *A61B 19/5244* (2013.01); *A61B 19/50* (2013.01); *A61B 2019/5268* (2013.01); *A61B 2018/00547* (2013.01); *G09B 23/30* (2013.01); *A61B 2017/00274* (2013.01); *A61B 2019/5255* (2013.01); *G09B 23/285* (2013.01); *A61B 2019/2292* (2013.01)
USPC .................. 434/262; 219/50; 219/53; 219/54; 219/602; 219/617; 434/236; 434/247; 345/633

(58) Field of Classification Search
CPC .................. A61B 2019/2292; A61B 19/5244; A61B 19/50; A61B 19/52; A61B 2019/5255; A61B 2017/00274; A61B 2018/00547; A61B 2019/5268; G09B 23/285; G09B 23/30
USPC ........ 219/50, 53, 54, 602, 603, 617; 434/236, 434/247, 633; 345/633
See application file for complete search history.

(56) References Cited

U.S. PATENT DOCUMENTS

| | | |
|---|---|---|
| 4,907,235 A | 3/1990 | Kuizenga |
| 5,130,997 A | 7/1992 | Ortiz et al. |
| 5,242,439 A | 9/1993 | Larsen et al. |
| 5,428,699 A | 6/1995 | Pon |
| 5,766,016 A | 6/1998 | Sinclair et al. |
| 5,882,206 A * | 3/1999 | Gillio ........................ 434/262 |

(Continued)

*Primary Examiner* — Jack Yip
(74) *Attorney, Agent, or Firm* — Westman, Champlin & Koehler, P.A.

(57) ABSTRACT

One embodiment of a Benign Prostate Hyperplasia (BPH) laser ablation simulator includes a frame, a mock hypotube, a mock laser fiber, a mock camera assembly, a laser fiber position tracker and a camera position tracker. The mock hypotube is supported by the frame, has a longitudinal axis, is received within the hypotube and is configured to move along the longitudinal axis and rotate about a laser fiber central axis relative to the hypotube. The mock camera assembly is attached to the hypotube and is configured to rotate about a camera central axis relative to the hypotube. The laser fiber position tracker is configured to output laser fiber position information that is indicative of a position of the mock laser fiber relative to the hypotube. The camera position tracker is configured camera position information that is indicative of a position of the mock camera assembly relative to the hypotube.

18 Claims, 8 Drawing Sheets

(56) References Cited

U.S. PATENT DOCUMENTS

| | | | |
|---|---|---|---|
| 5,951,301 A * | 9/1999 | Younker .................. 434/272 |
| 6,554,824 B2 | 4/2003 | Davenport et al. |
| 7,815,436 B2 | 10/2010 | Cunningham et al. |
| 2001/0016804 A1 * | 8/2001 | Cunningham et al. ............ 703/7 |
| 2001/0020178 A1 | 9/2001 | Arndt et al. |
| 2003/0032878 A1 * | 2/2003 | Shahidi .................. 600/429 |
| 2003/0091967 A1 * | 5/2003 | Chosack et al. ............... 434/262 |
| 2004/0045561 A1 * | 3/2004 | Alexander et al. ............ 128/897 |
| 2005/0203367 A1 * | 9/2005 | Ahmed et al. ................. 600/407 |
| 2006/0009751 A1 | 1/2006 | Zvuloni et al. |
| 2006/0122281 A1 | 6/2006 | Escandon et al. |
| 2007/0129712 A1 | 6/2007 | Neuberger |
| 2007/0225696 A1 | 9/2007 | Davenport et al. |
| 2007/0236514 A1 * | 10/2007 | Agusanto et al. ............. 345/646 |
| 2010/0273136 A1 | 10/2010 | Kandasami et al. |

* cited by examiner

BPH LASER ABLATION SIMULATION

CROSS-REFERENCE TO RELATED APPLICATION

This application claims the benefit of U.S. Provisional Application No. 61/475,870 filed Apr. 15, 2011. The above-referenced application is hereby incorporated by reference in its entirety.

BACKGROUND

Embodiments of the present invention are directed to systems and methods for simulating a Benign Prostate Hyperplasia (BPH) laser ablation treatment.

Benign Prostate Hyperplasia (BPH) is a condition wherein continued growth of the prostate restricts the passage of urine through the lower portion of the bladder and the urethra. BPH is often treated by surgically removing excess prostate tissue from the transitional zone of the prostate that is pressing on the urethra, which usually relieves the bladder outlet obstruction and incomplete emptying of the bladder caused by the BPH.

One procedure that is performed to remove excess prostate tissue involves vaporizing or ablating the targeted tissue using a surgical laser system. Such a system typically includes a laser energy source, an endoscope, such as a cystoscope or similar instrument (hereinafter "cystoscope"), a viewing fiber and a laser fiber. The laser fiber includes an optical fiber configured to deliver the laser energy from the laser energy source to targeted tissue of the prostate, and a side-firing probe tip at the distal end, which deflects laser energy sideways from a polished beveled surface or other conventional structure. The viewing fiber includes light and imaging guides for illuminating and imaging the tissue so that the clinician may direct the laser light and assess the progress and efficacy of the ablation procedure. The viewing fiber allows the surgeon to identify the targeted tissue, and view the ablation process. The cystoscope also has channels for supplying and removing an irrigant solution to and from the ablation site.

During the BPH laser ablation treatment, the clinician must carefully control the exposure of the targeted tissue to laser energy. This requires the placement of the distal tip of the laser fiber within 1-2 millimeters of the targeted tissue. The laser energy is delivered through the distal tip of the laser fiber as the laser fiber is moved by the clinician relative to the targeted tissue, such as by rotating the laser fiber by hand. If the laser fiber is moved too slowly, the targeted tissue may receive too high of a dosage of the laser energy, and if the laser fiber is moved too quickly, the targeted tissue may receive too low of a dosage of the laser energy.

To achieve clinical proficiency at performing the BPH laser ablation treatment, the clinician must practice the treatment. Typically, such practice involves the performance of the BPH laser ablation treatment on live or dead tissue using the actual laser surgical system. Unfortunately the availability of the laser surgical system for practice is often limited. Additionally, setting up the laser surgical system for the practice session, performing multiple practice BPH laser ablation treatments, assessing the performance of the clinician, and cleaning up the system can be time-consuming and costly.

SUMMARY

Embodiments of the invention are directed to a BPH laser ablation simulator. In one embodiment, the simulator comprises a frame, a mock hypotube, a mock laser fiber, a mock camera assembly, a laser fiber position tracker and a camera position tracker. The mock hypotube is supported by the frame and has a longitudinal axis. The mock laser fiber is received within the hypotube and is configured to move along the longitudinal axis and rotate about a laser fiber central axis relative to the hypotube. The mock camera assembly is attached to the hypotube and is configured to rotate about a camera central axis relative to the hypotube. The laser fiber position tracker is configured to output laser fiber position information that is indicative of a position of the mock laser fiber relative to the hypotube. The camera position tracker is configured camera position information that is indicative of a position of the mock camera assembly relative to the hypotube.

Other features and benefits that characterize embodiments of the present disclosure will be apparent upon reading the following detailed description and review of the associated drawings.

DETAILED DESCRIPTION OF ILLUSTRATIVE EMBODIMENTS

Embodiments of the invention are directed to a BPH laser ablation simulator that can be used to develop a user's skill to achieve clinical proficiency in performing BPH laser ablation treatments. Embodiments of the simulator closely emulate in real-time the look, feel and touch of an actual BPH laser ablation procedure. In one embodiment, the simulator can provide training modes to assist a clinician in practicing various aspects of the BPH laser ablation treatment. In one embodiment, the simulator assesses the performance of the clinician, such as tissue ablation measurements, to assist the clinician in determining their proficiency in the BPH laser ablation treatments.

Figure 1:
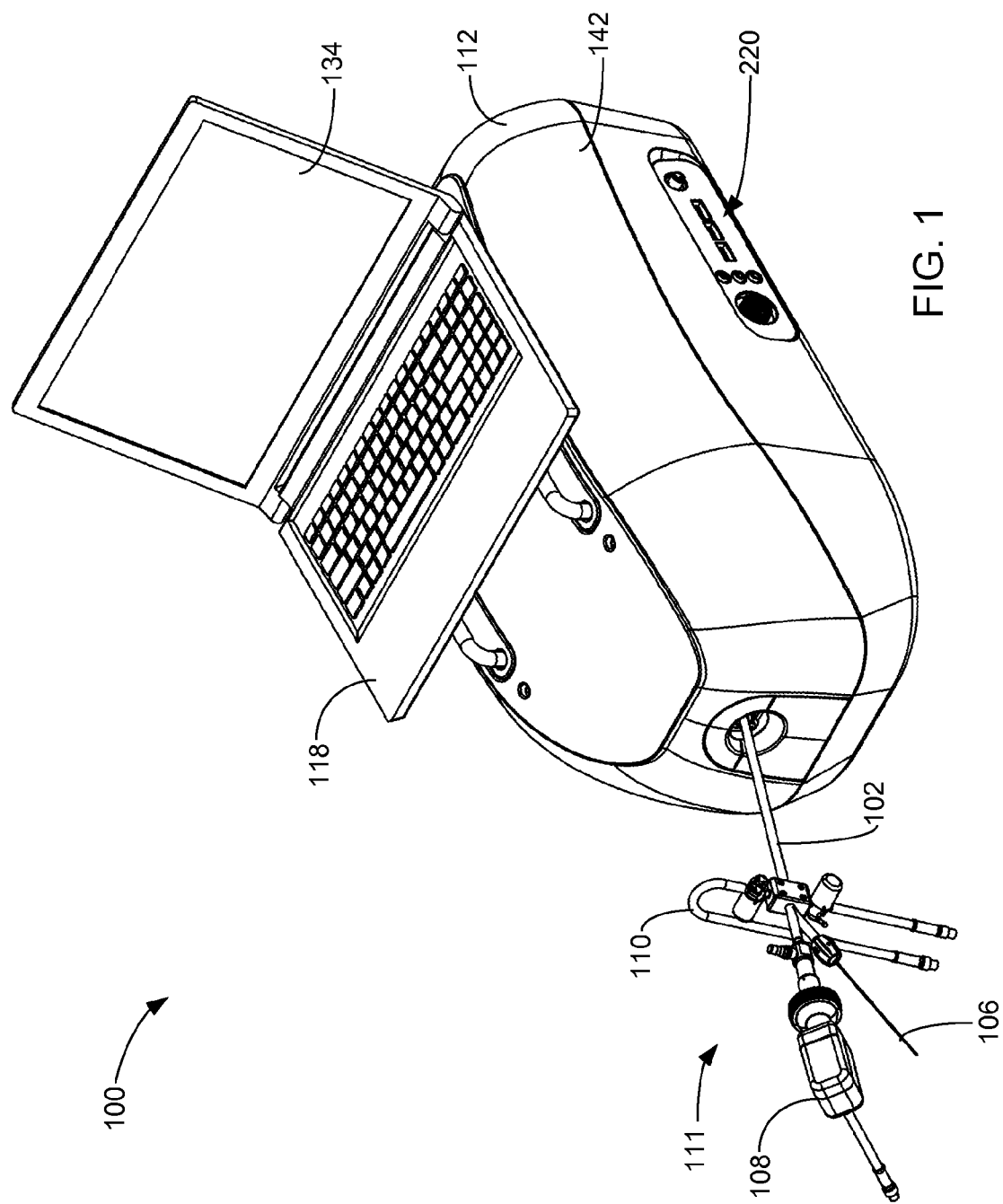
FIG. 1 is an isometric view of a BPH laser ablation simulator in accordance with embodiments of the invention.
Figure 2:
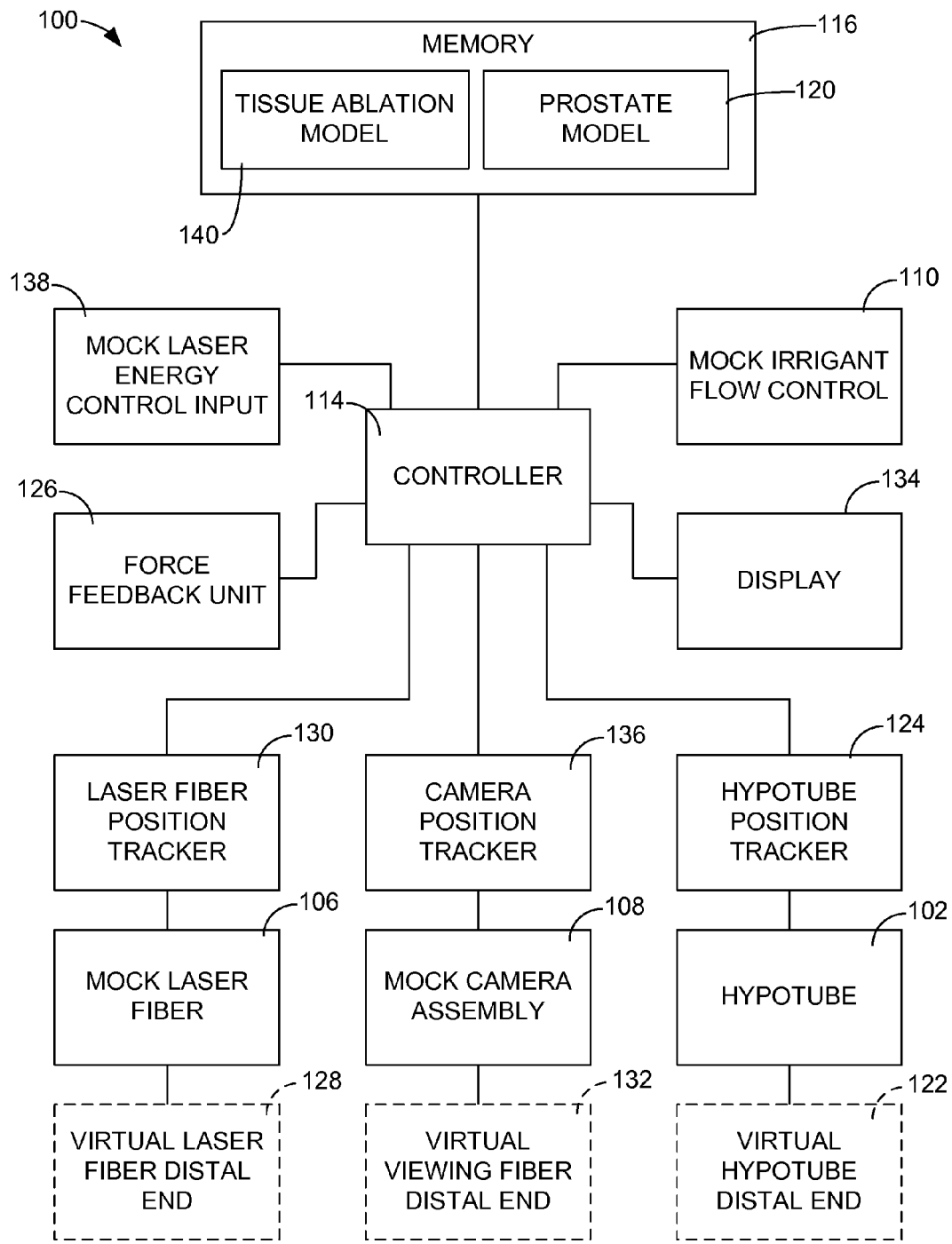
FIG. 2 is a simplified block diagram of a BPH laser ablation simulator in accordance with embodiments of the invention.

FIG. 1 is an isometric view of a BPH laser ablation or surgery simulator 100 and FIG. 2 is a simplified block diagram of the simulator 100 in accordance with embodiments of the invention. The simulator 100 allows a clinician to practice a BPH laser ablation treatment by controlling one or more mock components of an actual surgical laser system used to perform BPH ablation treatments. Embodiments of these mock components include, for example, a hypotube 102, a mock laser fiber 106, a mock camera assembly 108, and/or a mock irrigant flow control 110. These mock components are generally assembled into a mock cystoscope assembly 111, which is supported by a simulator unit 112.

In one embodiment, the mock laser fiber 106 provides the look and feel of laser fibers used in actual surgical laser systems, but does not deliver any actual laser energy to an ablation laser treatment target. In one embodiment, the mock laser fiber 106 does not include an optical fiber or other waveguide that would allow it to deliver actual laser energy.

In one embodiment, the mock camera assembly 108 represents the look and feel of an actual camera assembly. However, the mock camera assembly lacks the lighting and imaging components of an actual camera assembly used in surgical laser systems.

In one embodiment, the mock irrigant flow control provides the look and feel of actual irrigant flow controls used in conventional surgical laser systems, but is not configured to control an actual flow of irrigant through the hypotube 102. Rather, the irrigant flow control is used to control a virtual flow of irrigant through the hypotube.

In one embodiment, the simulator 100 includes a controller 114 comprising one or more processors configured to execute program instructions stored, for example, in the memory 116 for carrying out various process steps and functions described herein. The controller 114 may be implemented in multiple circuit boards located, for example, in the simulator unit 112, in a computer 118 (FIG. 1), and/or in one of the mock components of the simulator 100. The memory 116 represents one or more data storage components (i.e., RAM, ROM, flash memory, etc.) including local data storage components contained in, for example, the simulator unit 112 or the computer 118, or one or more remote data storage components that are accessible by the controller 114 through conventional data communication techniques, such as through a network.

In one embodiment, the simulator 100 includes a three-dimensional model 120 of the anatomy of a virtual human patient around the prostate (hereinafter "prostate model") 120 stored in the memory 116, as indicated in FIG. 2. The prostate model 120 can be any suitable conventional virtual patient model. In one embodiment, the prostate model 120 includes virtual tissue. In one embodiment, the prostate model 120 allows the simulator 100 to simulate various types of prostates, such as different sizes, to provide for a wide variety of treatment simulations, which can be selected through a suitable graphical user interface provided on the computer 118, for example. In one embodiment, the controller 114 translates the actual positions of the mock components relative to the simulator unit 112 or other real component of the simulator 100 to the coordinate system of the prostate model 120 to determine positions of corresponding virtual components within the prostate model 120.

In one embodiment, the hypotube 102 has a corresponding virtual hypotube distal end 122 that has a position within the prostate model 120 based on the position of the hypotube 102 relative to the simulator unit 112, such as a frame of the simulator unit 112. The position of the hypotube 102 is determined by the controller 114 using a hypotube position tracker 124, which outputs hypotube position information indicative of a position of the hypotube 102 relative to a frame of the simulator unit 112. The controller 114 adjusts a position of the virtual hypotube distal end 122 within, for example, the virtual urethra of the prostate model 120 responsive to movement of the hypotube 102 relative to the simulator unit 112.

In one embodiment, a force feedback unit 126 controls a force required to move the hypotube 102 relative to the simulator unit 112 based upon the position of the virtual hypotube distal end 122 within the prostate model 120. This provides the clinician with the feel that one would experience during an actual procedure.

In one embodiment, the mock laser fiber 106 has a corresponding virtual laser fiber distal end 128 through which virtual laser energy is discharged. Embodiments of the virtual laser fiber distal end 128 represent conventional probe tips, such as a side-firing probe tip that discharges the laser energy laterally relative to a central axis of the virtual laser fiber distal end 128. In one embodiment, the controller 114 determines a position of the virtual laser fiber distal end 128 within the prostate model 120 based on a position of the mock laser fiber 106 relative to the hypotube 102. In one embodiment, the simulator 100 includes a laser fiber position tracker 130 that outputs laser fiber position information indicative of a position of the mock laser fiber 106 relative to the hypotube 102 or a frame of the simulator unit 112. The controller 114 uses the laser fiber position information to determine the position of the virtual laser fiber distal end within the prostate model 120. The controller 114 moves the virtual laser fiber distal end 128 within the prostate model 120 responsive to movement of the mock laser fiber 106 relative to the hypotube 102. Thus, as with an actual surgical laser system, the clinician positions the virtual laser fiber distal end 128 proximate the virtual tissue targeted for ablation by moving the mock laser fiber 106 relative to the hypotube 102 by hand.

In one embodiment, the mock camera assembly 108 has a corresponding virtual viewing fiber distal end 132 at which a virtual imaging component is located. In one embodiment, the controller 114 produces images on a display 134 based on the location of the virtual viewing fiber distal end 132 within the prostate model 120, which is determined based on the position of the mock camera assembly 108 relative to the simulator unit 112 or hypotube 102. In one embodiment, the display 134 is provided by the computer 118, as shown in FIG. 1, or other conventional display.

In one embodiment, the simulator 100 includes a camera position tracker 136 that outputs camera position information indicative of a position of the mock camera assembly 108 relative to the hypotube 102 or a frame of the simulator unit 112. The controller 114 uses this camera position information to determine a position of the virtual viewing fiber distal end 132 within the prostate model 120. The image on the display 134 depicts portions of the virtual tissue of the prostate model 120 and possibly the virtual laser fiber distal end 128 that are within a field of view of the virtual imaging component at the virtual viewing fiber distal end 132 from its determined location within the prostate model 120. As the clinician adjusts the position of the camera assembly 108, the controller 114 responsively adjusts a position of the virtual viewing fiber distal end 132 within the prostate model 120 and adjusts the image on the display 118 accordingly, which simulates what occurs when using an actual surgical laser system. The clinician may identify virtual tissue of the prostate model 120 to be ablated through the adjustment of the position of the camera assembly 108 and the hypotube 102 and by viewing the images on the display 118.

In one embodiment, the system 100 includes a mock laser energy control input 138, such as foot pedal or other input, that is used by the clinician to trigger the delivery of virtual laser energy through the virtual laser fiber distal end 128. The controller 114 discharges the virtual laser energy through the virtual laser fiber distal end 128 responsive to signals from the laser energy control input 138. In one embodiment, the controller produces an image of the discharge of virtual laser energy from the virtual laser fiber distal end 128 on the display 118.

In one embodiment, the virtual laser energy has a wavelength of approximately 532 nanometers. This simulates the green laser energy produced by laser systems utilizing a yttrium-aluminum-garnet crystal rod with neodymium atoms dispersed in the YAG rod to form a Nd:YAG laser element.

In one embodiment, the controller 114 is configured to calculate changes to the properties of the virtual tissue of the prostate model that is exposed to the virtual laser energy, such as the degree and depth of the ablation, based on a tissue ablation model 140 stored in the memory 122. In one embodiment, the controller 114 determines the portions of the virtual tissue that have been exposed to the virtual laser energy based on the position of the virtual laser fiber distal end 128 relative to the virtual tissue and the spot size of the discharged virtual laser energy. In some embodiments, the laser energy dosage received by the exposed virtual tissue is then calculated based upon the duration of the exposure, the density of the virtual laser energy output from the virtual laser fiber tip, the distance the virtual tissue is displaced from the virtual laser fiber distal end, a wavelength of the virtual laser energy, and/or other parameters. In one embodiment, the controller 114 modifies the properties of the exposed virtual tissue in the prostate model 120 based on the determined effect of the exposure to the virtual laser energy. In one embodiment, the controller 114 modifies the image of the exposed virtual tissue produced on the display 118 based on changed properties.

In one embodiment, the controller 114 controls a flow of a virtual irrigant to the ablation site in response to a setting of the mock irrigant flow control 110 by the clinician. In one embodiment, the image provided on the display is based on the virtual irrigant flow. In one embodiment, the virtual flow of irrigant affects the changes in the properties of the virtual tissue responsive to the exposure to the virtual laser energy.

Figure 3:
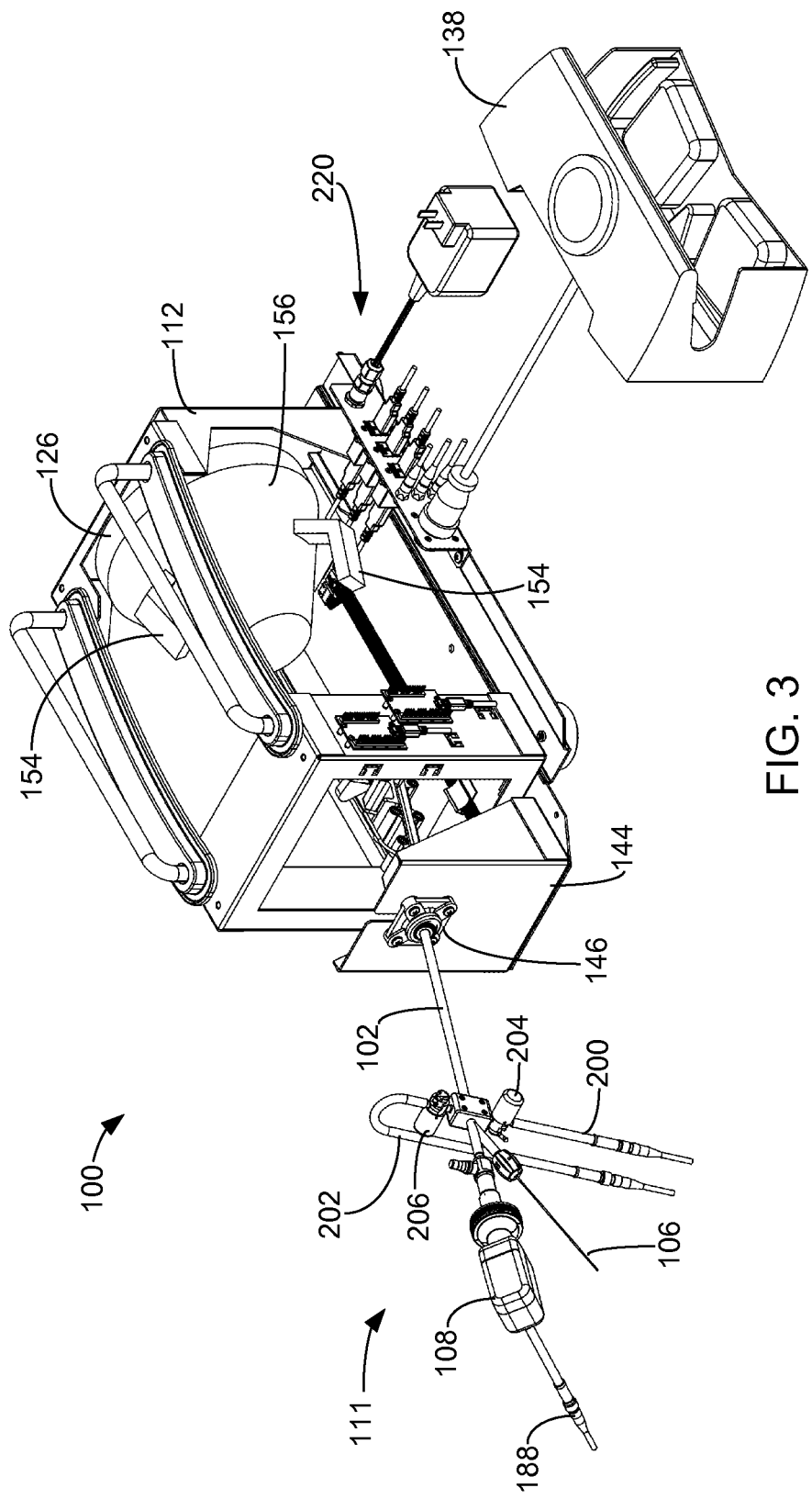
FIG. 3 is an isometric view of the simulator of FIG. 1 with some elements removed.
Figure 4:
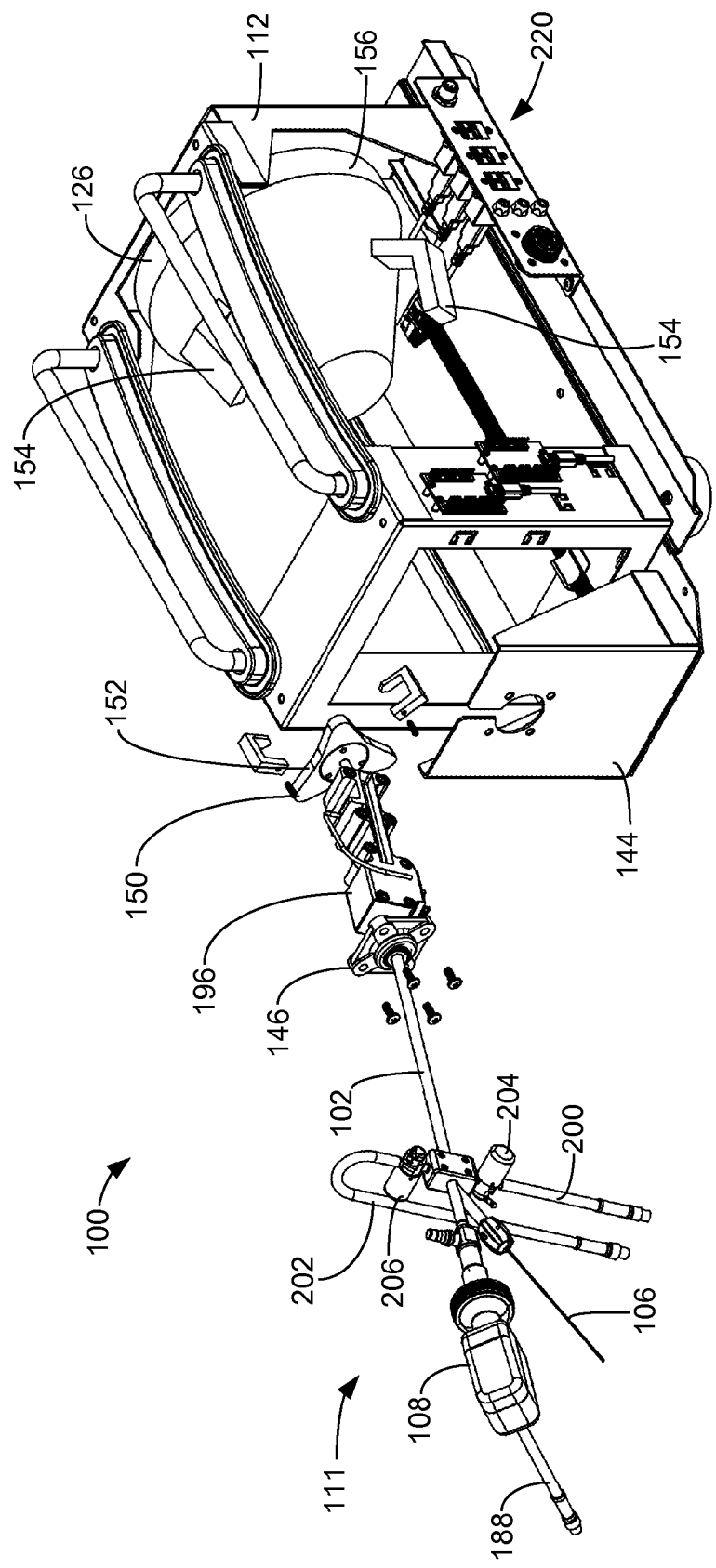
FIG. 4 is an isometric view of the cystoscope assembly exploded from the simulator of FIG. 3.
Figure 5:
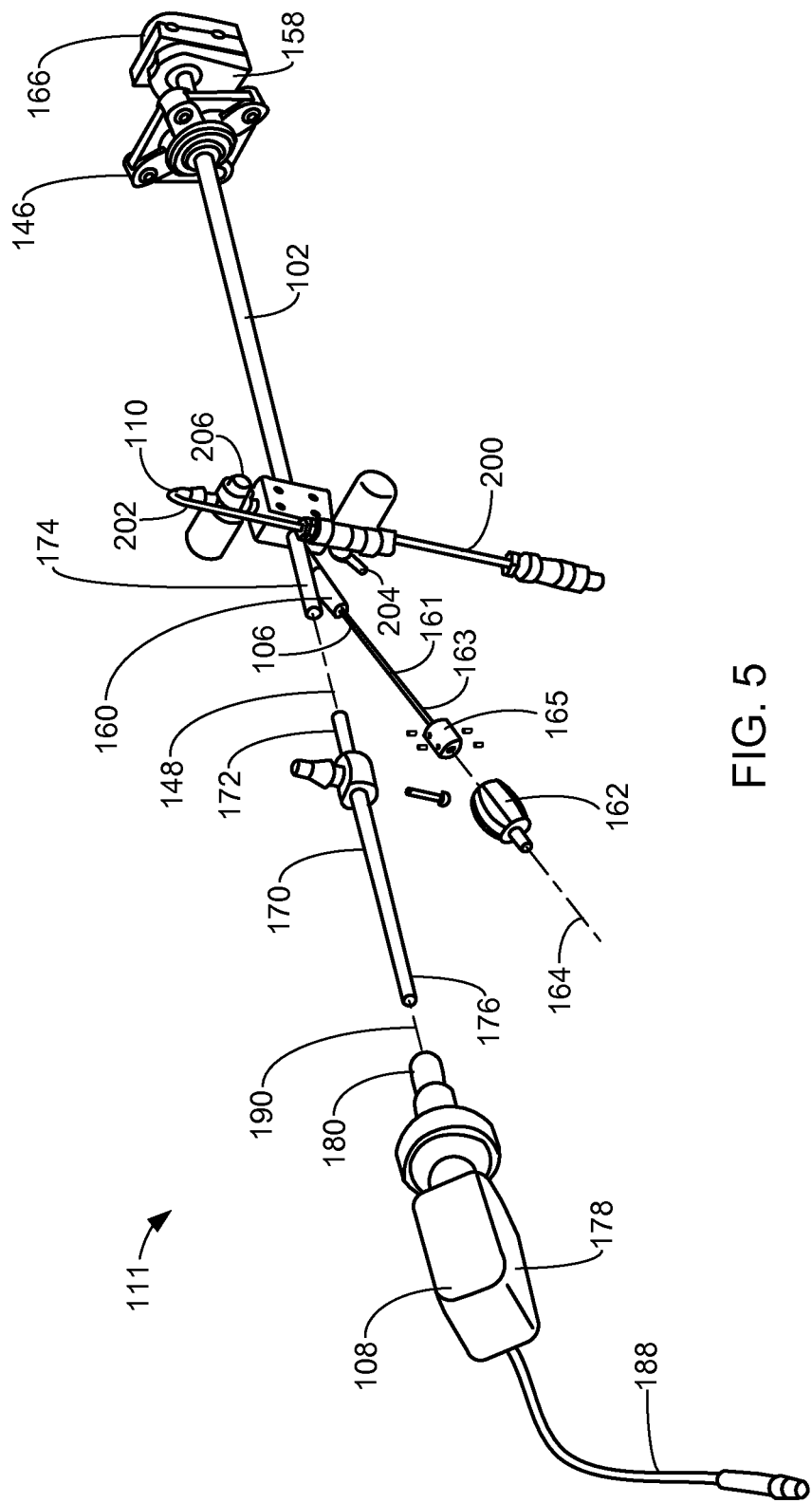
FIG. 5 is an exploded isometric view of a cystoscope assembly in accordance with embodiments of the invention.
Figure 6:
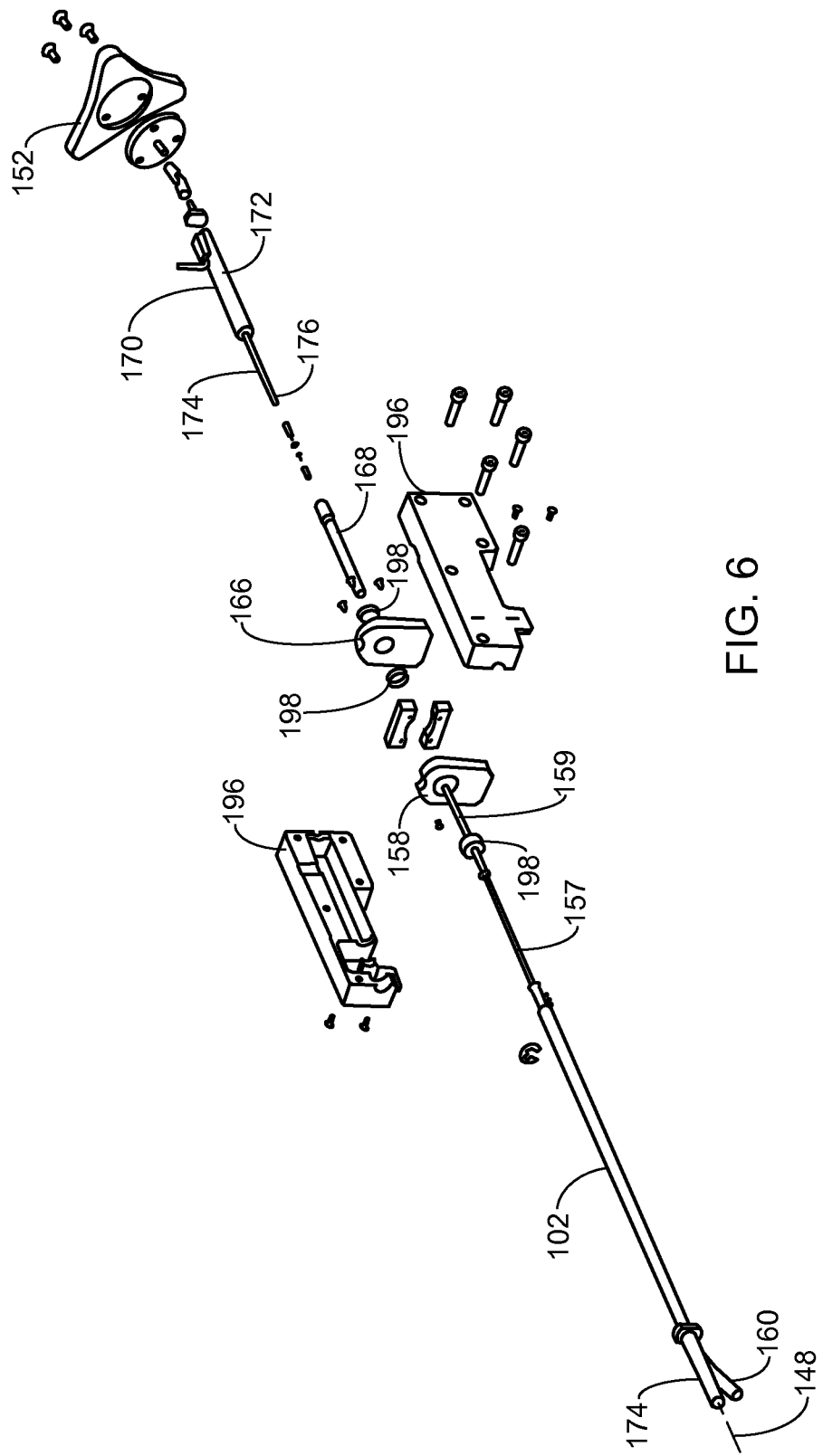
FIG. 6 is an exploded isometric view of a portion of the cystoscope assembly of FIG. 5 in accordance with embodiments of the invention.
Figure 7:
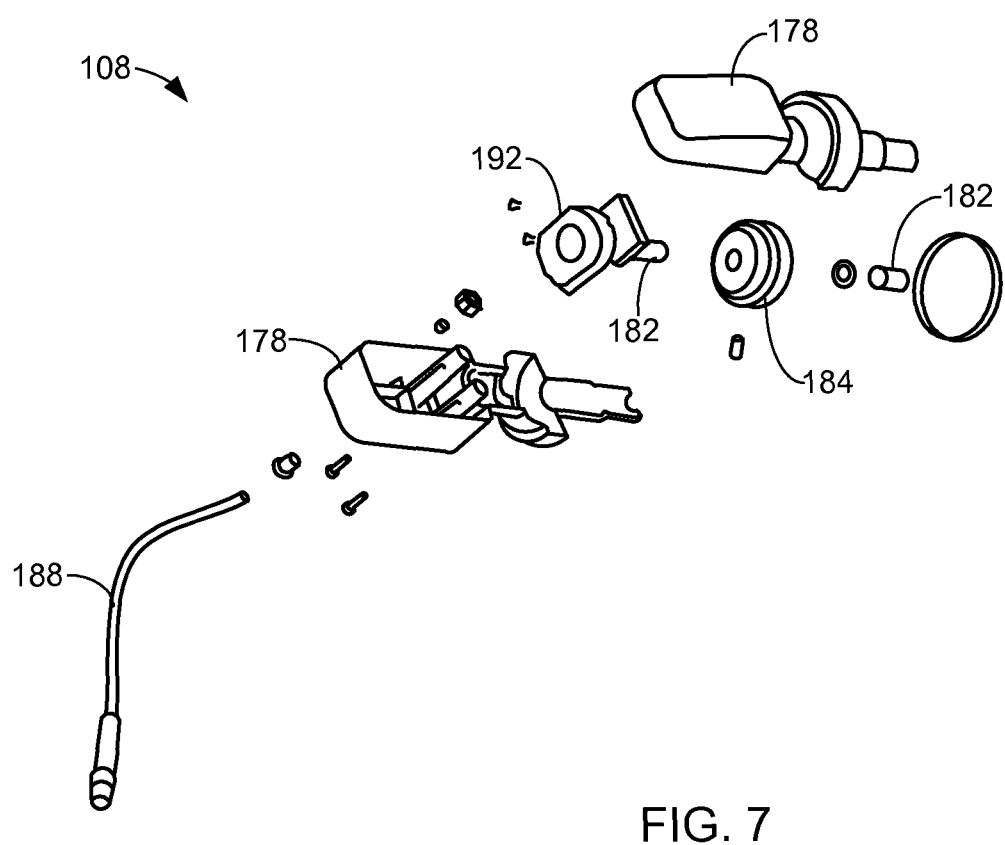
FIG. 7 is an exploded isometric view of a mock camera assembly in accordance with embodiments of the invention.
Figure 8:
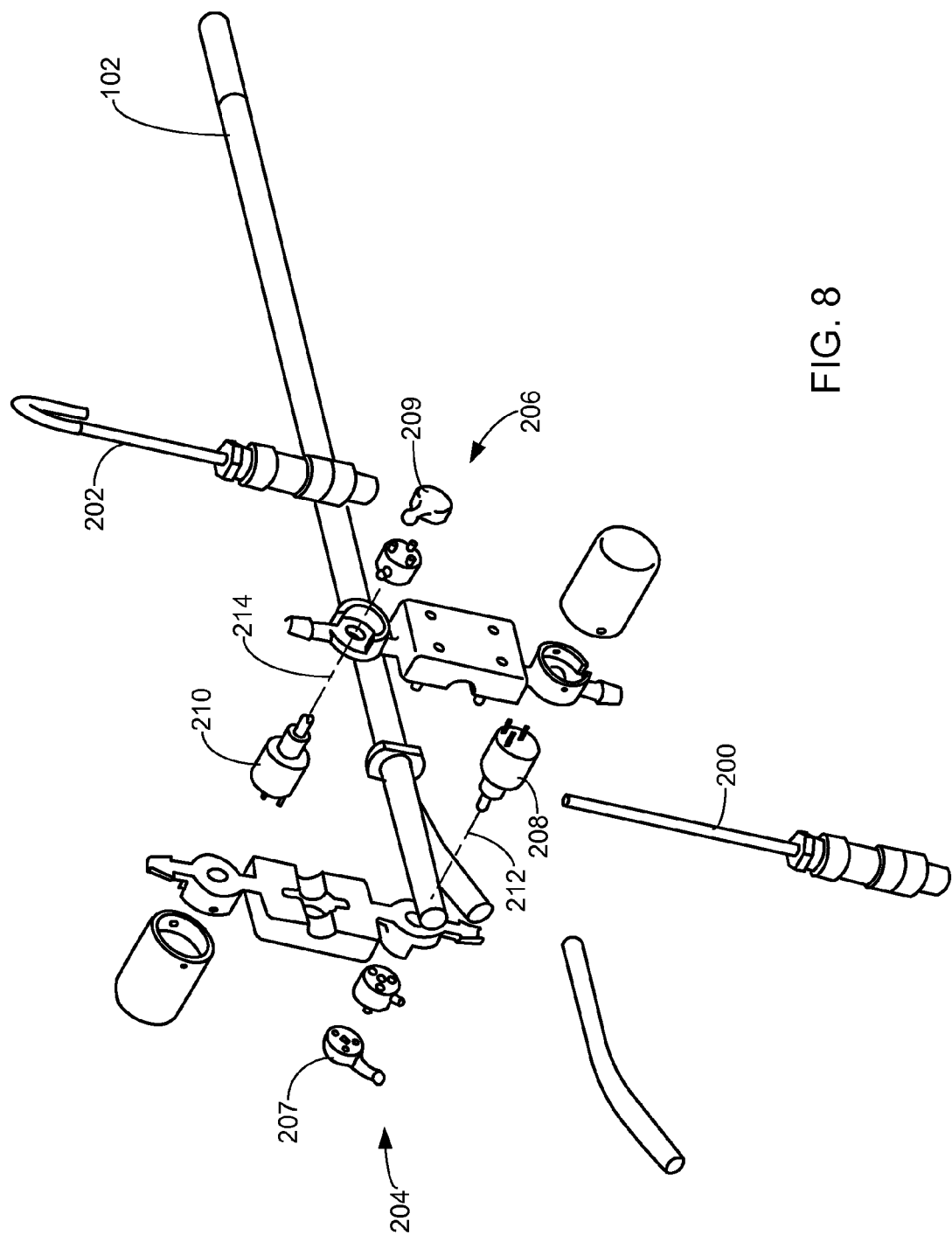
FIG. 8 is an exploded isometric view of a mock irrigant flow control in accordance with embodiments of the invention.

A detailed discussion of additional embodiments of the invention will be provided with reference to FIGS. 3-8. FIG. 3 is an isometric view of the simulator 100 without the computer 118 or the housing 142 of the simulator unit 112. FIG. 4 is an isometric view of the cystoscope assembly exploded from the simulator unit 112. FIG. 5 is an exploded isometric view of the cystoscope assembly 104 in accordance with embodiments of the invention. FIG. 6 is an exploded isometric view of a portion of the cystoscope assembly 111 in accordance with embodiments of the invention. FIG. 7 is an exploded isometric view of the mock camera assembly 108 in accordance with embodiments of the invention. FIG. 8 is an exploded isometric view of the mock irrigant flow control 110 in accordance with embodiments of the invention. Elements identified by reference numbers that are the same or similar to those discussed above correspond to the same or similar elements.

In one embodiment, the simulator unit 112 includes a frame 144 that supports the cystoscope assembly 111. In one embodiment, the hypotube 102 extends through a pivotal coupling 146 that is attached to the frame 144. Pivotal coupling 146 allows the hypotube 102 to pivot and move along a longitudinal axis 148 (FIG. 5) relative to the frame 144. In one embodiment, the pivotal coupling 146 also allows the hypotube 102 to rotate about the longitudinal axis 148 relative to the frame 144. In one embodiment, the pivotal coupling 146 comprises a ball and socket joint and the hypotube extends through the ball component, as shown in FIG. 5.

In one embodiment, a distal end 150 of the cystoscope assembly 111 includes a member 152 (FIGS. 4 and 6) that couples to the force feedback unit 126. In one embodiment, the force feedback unit 126 is a conventional device having three arms 154 that extend toward the cystoscope assembly 111 and attach to the member 152. The arms 154 are configured to move relative to a main body 156 of the force feedback unit 126. The force required to move the arms 154 relative to the main body 156 is varied by the force feedback unit 126 based on various factors described herein using the controller 114. One exemplary force feedback unit 126 that is suitable for use in the simulator 100 is the Novint Falcon, a USB 2.0 haptic device using the Jacobian mathematic function to determine the location of a graphical element in a three-dimensional space in computer software applications with position resolution of greater than 400 dpi. The internal motors of the Falcon can be applied in any direction with maximum force capabilities of over 2 lbs.

In one embodiment, the hypotube position tracker 124 includes the force feedback unit 126. The arms 154 attached to the member 152 move in response to the pivoting of the hypotube 102 and movement of the hypotube 102 along the longitudinal axis 148 relative to the frame 144. In one embodiment, the force feedback unit 126 determines the position and orientation of the hypotube 102 relative to the frame 144 based on a position of the arms 154 relative to the main body 156. This hypotube position information is output to the controller 114 and is used by the controller 114 to determine a position and orientation of the virtual hypotube distal end 122 relative to the prostate model. In one embodiment, the position of the virtual hypotube distal end 122 within the prostate model 120 determines the amount of force required to move the arms 154 and, thus, the force required to pivot the hypotube 102 and move the hypotube 102 along the longitudinal axis 148 relative to the frame 144 of the simulator unit 112.

One embodiment of the hypotube position tracker 124 is configured to output hypotube position information that includes angular position information indicative of an angular position of the hypotube 102 measured about the longitudinal axis 148 relative to the frame 144 of the simulator unit 112 or other reference. In one embodiment, a rod 157 (FIG. 6) is received within the hypotube 102 and rotates about the longitudinal axis 148 responsive to rotation of the hypotube 102 about the axis 148. In one embodiment, the hypotube position tracker 124 includes an encoder 158 that receives a keyed portion 159 of the rod 157. Rotation of the hypotube 102 about the longitudinal axis 148 causes the keyed portion 159 of the rod 157 to rotate about the longitudinal axis 148, which in turn drives an encoder wheel or gear within the encoder 158. The rotation of the encoder wheel or gear within the encoder 158 is used to determine an angular position of the hypotube 102 about the longitudinal axis 148 relative to a reference. The encoder 158 outputs the angular position of the hypotube to the controller 114, which uses the information to determine the position of the virtual hypotube distal end 122 relative to the prostate model 120.

The mock laser fiber 106 is received within the hypotube 102, such as through a port 160, as shown in FIG. 5. In one embodiment, the mock laser fiber 106 comprises a wire 161, such as a wire formed of Nitinol (NiTi). In one embodiment, a grip 162 is attached to a proximal end 163 of the mock laser fiber 106 and can be used by the clinician to rotate the mock laser fiber 106 about its central axis 164 and move the mock laser fiber 106 in and out of the hypotube 102 in the direction of the laser fiber central axis 164 and along the longitudinal axis 148 of the hypotube 102. In one embodiment, the grip 162 includes a stop 165 that limits the distance the mock laser fiber 106 may be inserted through the port 160 of the hypotube 102.

As mentioned above, the laser fiber position tracker 130 is configured to output laser fiber position information that indicates a position of the mock laser fiber 106 relative to the hypotube 102 or a frame, such as frame 144, of the simulator unit 112. This laser fiber position information is used by the controller 114 to determine a position and orientation of the virtual laser fiber distal end 128 within the prostate model 120. In one embodiment, the laser fiber position information includes laser fiber angular position information that is indicative of an angular position of the mock laser fiber 106 measured about the laser fiber central axis 164 relative to the hypotube 102 or other reference.

In one embodiment, the laser fiber position tracker 130 comprises an encoder 166, through which the wire 161 of the mock laser fiber 106, or a component coupled to the wire 161 extends. In one embodiment, the wire 161 couples to a component 168 that is keyed to an encoder wheel or gear of the encoder 166. Rotation of the wire 161 of the mock laser fiber 106 about the laser fiber central axis 164 causes the component 168 to rotate about the laser fiber central axis 164 and generally about the longitudinal axis 148. Rotation of the component 168 drives the rotation of an encoder wheel or gear of the encoder 166. The encoder 166 outputs the laser fiber angular position information to the controller 114, which is based on the angular position of the encoder wheel or gear relative to a reference. One suitable encoder for use as encoder 166 is CUI Inc's AMT 102-V vertical modular 16RES SW TTL Radial capacitive encoder. Other encoders or similar components can be used to produce the laser fiber angular position information responsive to rotation of the wire 161 of the mock laser fiber 106.

In one embodiment, the laser fiber position information output by the laser fiber position tracker 130 includes laser fiber longitudinal position information that is indicative of a position of the mock laser fiber 106 measured along the longitudinal axis 148 relative to the hypotube 102 or other reference. In one embodiment, the wire 161 of the mock laser fiber 106 is connected to a linear potentiometer 170, shown in FIG. 6. The linear potentiometer 170 comprises a main body 172 and a rod 174, which is configured to move along the longitudinal axis 148 relative to the main body 172. The rod 174 includes a proximal end 176, to which the wire 161 or an extension thereof, is attached. Movement of the mock laser fiber 106 relative to the hypotube 102 along the laser fiber central axis 164 or the longitudinal axis 148 drives movement of the rod 174 relative to the main body 172. The position of the rod 174 relative to the main body 172 indicates a position of the mock laser fiber 106 relative to the hypotube 102, or an amount that the wire 161 of the mock laser fiber 106 has been inserted into the hypotube 102. The linear potentiometer 170 outputs the laser fiber longitudinal position information based on the position of the rod 174 relative to the main body 172. The controller 114 uses the laser fiber longitudinal position information to determine a location of the virtual laser fiber distal end 128 within the prostate model 120. The laser fiber position tracker 130 can use alternative devices and components to produce the laser fiber longitudinal position information.

In one embodiment, the mock camera assembly 108 is mounted to the hypotube 102 using a rod 170. A distal end 172 of the rod 170 is received within a port 174 of the hypotube 102, as shown in FIG. 5. A proximal end 176 of the rod 170 is received within the mock camera assembly 108. In one embodiment, the mock camera assembly 108 includes a housing 178 having a receiving end 180 through which the proximal end 176 of the rod 170 is inserted. In one embodiment, the mock camera assembly 108 includes bearings 182 through which the proximal end 176 of the rod 170 extends. In one embodiment, a weight 184 is attached to the housing 178. The weight 184 and the bearings 182 allow the mock camera assembly 108 to have the feel of a camera assembly used in actual surgical laser systems. In one embodiment, the mock camera assembly 108 includes an output cable 188 that attaches to the housing 178, but does not provide an output signal from an imaging component.

As mentioned above, the camera position tracker 136 is configured to output camera position information indicative of a position of the mock camera assembly 108 relative to the hypotube 102 or other reference. In one embodiment, the camera position information includes camera angular position information that is indicative of an angular position of the mock camera assembly 108 measured about a camera central axis 190, shown in FIG. 5. The camera central axis 190 is generally coaxial to the longitudinal axis 148 of the hypotube 102, when the camera assembly 108 is attached to the port 174 using the rod 170. In one embodiment, the mock camera assembly 108 includes an encoder 192 that receives the proximal end 176 of the rod 170. In one embodiment, the angular position of the rod 170 is fixed relative to the hypotube 102 and rotation of the mock camera assembly 108 about the camera central axis 190 relative to the rod 170 and the hypotube 102 drives rotation of an encoder wheel or gear within the encoder 192. The angular position of the encoder wheel or gear within the encoder 192 relative to a reference provides the camera position information, which is output to the controller 114 and used by the controller 114 to determine the angular position of the virtual viewing fiber distal end 132 within the prostate model 120.

In one embodiment, the encoders 158 and 166, the component 168 and the linear potentiometer 170 are contained within a housing 196, as shown in FIGS. 4 and 6. Bearings 198 facilitate rotation of the hypotube 102 and component 168 relative to the housing 196.

In one embodiment, the mock irrigant flow control 110 is coupled to the hypotube 102, as shown in FIG. 5. The components forming the mock irrigant flow control 110 generally have the same appearance as their real counterparts used in actual surgical laser systems. Thus, embodiments of the irrigant flow control 110 include a mock input tube 200 and a mock output tube 202. In one embodiment, the mock irrigant flow control 110 includes a mock input flow control valve 204 and a mock output flow control valve 206, which respectively simulate valves used to control irrigant flow to and from the ablation site through the cystoscope assembly 111.

In one embodiment, the control valve 204 has a control knob 207 and an encoder 208, and the control valve 206 has a control knob 209 and an encoder 210. In one embodiment, the knob 207 is configured to rotate about an axis 212 and the knob 209 is configured to rotate about an axis 214. The rotation of the knob 207 about the axis 212 is registered by the encoder 208, which outputs valve position signals indicative of an angular position of the knob 207 relative to a reference Likewise, rotation of the knob 209 about the axis 214 is registered by the encoder 210, which outputs valve position signals indicative of an angular position of the knob 209 relative to a reference. The controller 114 uses the valve position signals to determine input and output flows of virtual irrigant to the ablation site through the cystoscope assembly 111. In one embodiment, the controller 114 controls the image produced on the display 134 and/or the virtual ablation process based on the irrigant flow control settings determined by the position of the switches 204 and 206.

In one embodiment, the position information output from the encoders (e.g., 158, 166, 192, 208, 210) and the linear potentiometer 170, and the signals from the control input 138 are delivered to the controller through various inputs 220 on the simulator unit 112. In one embodiment, the cables feeding the information from at least some of these components mimic cabling or tubing of actual surgical laser systems. For instance, in one embodiment, the camera angular position information output from the encoder 192 is provided through the output cable 188 which may be connected to one of the inputs 220 shown in FIG. 3.

Another embodiment of the invention is directed to a method of simulating a BPH laser ablation treatment using the simulator 100. In one embodiment, a simulator 100 formed in accordance with one or more of the embodiments described above is provided. In one embodiment, a viewing fiber position corresponding to a position of a virtual viewing fiber distal end 132 within a coordinate system of the prostate model 120 is determined based on a position of the mock camera assembly 108 relative to the hypotube 102 using the controller 114. In one embodiment, this position information is output by the viewing fiber position tracker 136 formed in accordance with one or more embodiments described above.

In one embodiment, an image is produced on the display 134 based upon the prostate model 120 and the viewing fiber position using the controller 114. As discussed above, the controller 114 is configured to determine a view from a virtual imaging component located at the virtual viewing fiber distal end 122 based on the viewing fiber position information produced by the viewing fiber position tracker 136. The viewing fiber position may also be dependent on the position of the hypotube 102 relative to the frame 144 of the simulator unit 112. This position information may be output from the hypotube position tracker 124, as discussed above. Based on the viewing fiber position and orientation within the prostate model 120, the controller produces the image on the display 134 that simulates a view from the virtual imaging component located at the virtual viewing fiber distal end 132, using conventional techniques.

In one embodiment of the method, the mock camera assembly 108 is moved by a clinician. This results in a change in the position of the virtual viewing fiber distal end 132 within the prostate model 120. In one embodiment, the controller 114 determines the new position of the virtual viewing fiber distal end 132 based on position information output from the viewing fiber position tracker 136 and produces a new image on the display 134 accordingly.

In accordance with another embodiment of the method, a position and orientation of a virtual laser fiber distal end 128 within the coordinate system of the prostate model 120 is determined based on a position of the mock laser fiber 106 relative to the hypotube 102 using the controller 114. As discussed above, the position of the mock laser fiber 106 relative to the hypotube 102 may be determined using the laser fiber position tracker 130. In one embodiment, a virtual dose of laser energy is delivered to tissue of the prostate model proximate the virtual laser fiber distal end 128 responsive to an input from a user of the simulator 100. In one embodiment the input is received by the controller 114 from a mock laser energy control input 138, such as a foot pedal, as shown in FIG. 3. In one embodiment, properties of the tissue are adjusted based on the virtual dose of laser energy delivered to the tissue using the controller 114. In one embodiment, the controller 114 determines the change in the properties of the tissue using a tissue ablation model 140 stored in memory 116, as discussed above.

In accordance with another embodiment, the mock laser fiber 106 is moved during the delivery of the virtual dose of laser energy. This exposes different portions of the virtual tissue of the prostate model 120 to virtual doses of the laser energy.

In one embodiment, a force required to move the hypotube 102 relative to the frame 144 is adjusted in response to the changing properties of the tissue of the prostate model 120 due to the exposure to the laser energy. For instance, portions of the virtual tissue exposed to doses of the virtual laser energy become virtually ablated or vaporized in accordance with the tissue ablation model 140. The controller adjusts the force required to move the hypotube 102 relative to the frame 144 using the force feedback unit 126 to simulate the change a clinician would feel during an actual BPH laser ablation treatment.

One embodiment of the simulator 100 provides training exercises relating to BPH laser ablation treatments using the controller 114. In one embodiment, the simulator 100 provides a sweep speed training exercise having an objective to keep the virtual laser beam output from the virtual laser fiber distal end 128 centered on a target that moves at a predetermined speed, such as 3 mm per second, for as long as possible. This allows the clinician to practice moving the mock laser fiber 106 at a speed that is desired to provide optimum laser ablation for a given type of laser energy (e.g., 532 nm).

In one embodiment of the sweep speed training exercise, a BPH laser surgery simulator 100 formed in accordance with one or more embodiments described herein is provided. In one embodiment, the simulator 100 comprises a mock hypotube 102, a mock laser fiber 106, a display 134 and a controller 114. The mock hypotube is supported by a frame 144 and has a longitudinal axis 148. The hypotube 102 is configured to move relative to the frame 144. The mock laser fiber is received within the hypotube 102 and is configured to move along the longitudinal axis 148 and rotate about a laser fiber central axis 162 relative to the hypotube 102.

In one embodiment of the sweep speed training exercise, a target image is moved on the display 134 using the controller 114. The mock laser fiber 106 is moved relative to the hypotube 102 by a clinician. A virtual laser beam is then moved on the display 134 responsive to the movement of the mock laser fiber using the controller 114. As discussed above, this is generally accomplished by determining changes in the position of the mock laser fiber 106 using the laser fiber position tracker 130. In one embodiment of the method, a score is determined based on the virtual laser beam striking the target image using the controller 114. In one embodiment, the longer the period during which the virtual laser beam strikes the target image, the greater the score.

Another training exercise that can be performed using the simulator 100 is a tissue distance simulation. In accordance with this embodiment, the simulator 100 trains the clinician to maintain the virtual laser fiber distal end 128 approximately 0.5-2.5 mm from the virtual tissue of the prostate model 120. This distance is generally optimal for tissue ablation. The objective of this training exercise is to obtain as much tissue ablation as possible. In one embodiment, the controller 114 assesses a score based upon the positioning of the virtual laser fiber distal end 128 relative to the virtual tissue of the prostate model 120 targeted for ablation over a predetermined exercise period, such as two minutes.

In accordance with another embodiment, the simulator 100 provides an anatomy identification exercise. The objective of this exercise is to identify and verify knowledge of the anatomical landmarks of the prostate model presented on the display 134 responsive to the positioning of the virtual viewing fiber distal end 132 through movement of the mock camera assembly 108 by the clinician. In one embodiment, the clinician is prompted by the simulator 100 to deliver virtual laser energy to an anatomical landmark. Such a prompt may be presented on the display 134 in accordance with program instructions executed by the controller 114. Points are awarded to the clinician for accurately delivering a dose of virtual laser energy through the virtual laser fiber distal end 128 to the correct anatomical landmark. Points may also be awarded based on how quickly the clinician delivers the laser energy to the correct anatomical landmark.

Although the present invention has been described with reference to preferred embodiments, workers skilled in the art will recognize that changes may be made in form and detail without departing from the spirit and scope of the invention. For example, the movement of the mock components may be measured relative to other components of the system 100 described above.

What is claimed is:

1. A benign prostate hyperplasia (BPH) laser surgery simulator comprising:
    a frame;
    a mock hypotube supported by the frame and having a longitudinal axis, wherein the mock hypotube is configured to pivot and move along the longitudinal axis relative to the frame;
    a hypotube tracker configured to output hypotube position information indicative of a position of the hypotube relative to the frame;
    a mock laser fiber received within the hypotube configured to move along the longitudinal axis and rotate about a laser fiber central axis relative to the hypotube;
    a laser fiber position tracker configured to output laser fiber position information indicative of a position of the mock laser fiber relative to the hypotube;
    a mock camera assembly attached to the hypotube configured to rotate about a camera central axis relative to the hypotube; and
    a camera position tracker configured to output camera position information indicative of a position of the mock camera assembly relative to the hypotube.

2. The simulator of claim 1, further comprising a force feedback unit coupled to a distal end of the hypotube and configured to vary a force required to move the hypotube.

3. The simulator of claim 2, wherein the hypotube tracker includes the force feedback unit, which provides the hypotube position information including a location of a distal end of the hypotube relative to the frame.

4. The simulator of claim 1, wherein the hypotube position information includes angular position information indicative of an angular position of the hypotube measured about the longitudinal axis relative to the frame.

5. The simulator of claim 1, wherein the laser fiber position information includes:
    laser fiber angular position information indicative of an angular position of the laser fiber measured about the laser fiber central axis relative to the hypotube; and
    laser fiber longitudinal position information indicative of a position of the laser fiber measured along the longitudinal axis relative to the hypotube.

6. The simulator of claim 5, wherein the laser fiber comprises a wire at a proximal end, the wire having a distal end coupled to a potentiometer of the laser fiber position tracker configured to output the laser fiber longitudinal position information.

7. The simulator of claim 5, wherein the laser fiber comprises a wire at a proximal end, and the wire extends through an encoder of the laser fiber position tracker configured to output the laser fiber angular position information.

8. The simulator of claim 1, wherein the camera position information includes camera angular position information indicative of an angular position of the camera assembly measured about the camera central axis relative to the hypotube.

9. The simulator of claim 8, further comprising an encoder configured to sense rotation of the camera assembly and output the camera angular position information.

10. The simulator of claim 1, further comprising a mock irrigant flow control coupled to the mock hypotube, the irrigant flow control comprising a mock input flow control valve and a mock output flow control valve, each configured to generate valve position signals indicative of a position of the valves.

11. The simulator of claim 1, further comprising:
    a memory;
    a prostate model stored in the memory comprising a three-dimensional model of a prostate and surrounding anatomy;
    a display; and
    a controller comprising one or more processors configured to control the display based on the hypotube position information, the camera position information and the prostate model.

12. The simulator of claim 11, wherein:
    the simulator further comprises a force feedback unit coupled to a distal end of the mock hypotube; and
    the controller is configured to control the force feedback unit to vary a force required to move the hypotube relative to the frame based on the hypotube position information, the camera position information and the prostate model.

13. The simulator of claim 12, wherein:
    the simulator further comprises a tissue ablation model stored in the memory, the tissue ablation model defining changes to tissue of the prostate model responsive to exposure to laser energy; and
    the controller is configured to adjust properties of tissue of the prostate model based on exposure to virtual doses of laser energy using the tissue ablation model, and control the force feedback unit to vary the force required to move the hypotube relative to the frame based on the properties of the tissue.

14. The simulator of claim 13, wherein the controller is configured to adjust properties of tissue of the prostate model based on exposure to virtual doses of laser energy having a wavelength of approximately 532 nanometers using the tissue ablation model.

15. A method comprising:
    providing a benign prostate hyperplasia (BPH) laser surgery simulator comprising:
        a mock hypotube supported by a frame and having a longitudinal axis;
        a mock laser fiber received within the hypotube configured to move along the longitudinal axis and rotate about a laser fiber central axis relative to the hypotube;
        a mock camera assembly attached to the hypotube configured to rotate about a camera central axis relative to the hypotube;
        a memory containing a prostate model comprising a three-dimensional model of a prostate and surrounding anatomy;
        a display; and
        a controller comprising one or more processors;

determining a viewing fiber position corresponding to a position of a virtual viewing fiber distal end within a coordinate system of the prostate model based on a position of the camera assembly relative to the hypotube using the controller;

displaying an image on the display based upon the prostate model and the viewing fiber position, using the controller;

moving the mock camera assembly;

changing the image on the display responsive to moving the mock camera assembly;

determining a position and orientation of a virtual laser fiber distal end within the coordinate system of the prostate model based on a position of the mock laser fiber relative to the hypotube using the controller;

delivering a virtual dose of laser energy to tissue of the prostate model proximate the virtual laser fiber distal end responsive to input from a user of the simulator; and adjusting properties of the tissue based on the virtual dose of laser energy based upon a tissue ablation model using the controller.

16. The method of claim 15, further comprising:

moving the mock laser fiber during delivering a virtual dose of laser energy; and exposing different portions of the tissue to different virtual doses of laser energy responsive to moving the mock laser fiber.

17. The method of claim 15, further comprising adjusting a force required to move the hypotube relative to the frame responsive to adjusting properties of the tissue using a force feedback unit.

18. A method comprising:

providing a BPH laser surgery simulator comprising:

a frame;

a mock hypotube supported by a frame and having a longitudinal axis, the hypotube configured to move relative to the frame;

a hypotube tracker configured to output hvpotube position information indicative of a position of the hvpotube relative to the frame;

a mock laser fiber received within the hypotube configured to move along the longitudinal axis and rotate about a laser fiber central axis relative to the hypotube;

a laser fiber position tracker configured to output laser fiber position information indicative of a position of the mock laser fiber relative to the hypotube;

a mock camera assembly attached to the hvpotube configured to rotate about a camera central axis relative to the hvpotube;

a camera position tracker configured to output camera position information indicative of a position of the mock camera assembly relative to the hvpotube;

a display; and a controller comprising one or more processors;

moving a target image on the display using the controller;

moving the mock laser fiber relative to the hypotube;

moving a virtual laser beam on the display responsive to moving the mock laser fiber based on the laser fiber position information using the controller; and determining a score based on the virtual laser beam striking the target image using the controller.

\* \* \* \* \*

UNITED STATES PATENT AND TRADEMARK OFFICE
CERTIFICATE OF CORRECTION

Page 1 of 1

PATENT NO. : 8,932,063 B2
APPLICATION NO. : 13/446551
DATED : January 13, 2015
INVENTOR(S) : Taylor et al.

It is certified that error appears in the above-identified patent and that said Letters Patent is hereby corrected as shown below:

IN THE SPECIFICATION:
In Column 4, Line 52, delete "display 118" and insert -- display 134 --, therefor; In Column 4, Line 57, delete "display 118." and insert -- display 134. --, therefor; In Column 4, Line 67, delete "display 118." and insert -- display 134. --, therefor.

In Column 5, Line 10, delete "memory 122." and insert -- memory 116. --, therefor; In Column 5, Line 26, delete "display 118" and insert -- display 134 --, therefor.

In Column 7, Line 57, delete "distal end 172" and insert -- distal end 128 --, therefor; In Column 7, Line 58, delete "port 174" and insert -- port 160 --, therefor.

In Column 8, Lines 15-16, delete "port 174" and insert -- port 160 --, therefor; In Column 8, Line 52, delete "reference" and insert -- reference. --, therefor.

In Column 9, Line 18, delete "tracker 136" and insert -- tracker 130 --, therefor; In Column 9, Line 26, delete "tracker 136." and insert -- tracker 130. --, therefor; In Column 9, Line 42, delete "tracker 136" and insert -- tracker 130 --, therefor.

In Column 10, Line 32, delete "axis 162" and insert -- axis 164 --, therefor.

IN THE CLAIMS:
In Column 14, Line 7, in Claim 18, delete "hvpotube" and insert -- hypotube --, therefor; In Column 14, Lines 8-9, in Claim 18, delete "hvpotube" and insert -- hypotube --, therefor; In Column 14, Line 17, in Claim 18, delete "hvpotube" and insert -- hypotube --, therefor; In Column 14, Line 19, in Claim 18, delete "hvpotube;" and insert -- hypotube; --, therefor; In Column 14, Line 22, in Claim 18, delete "hvpotube;" and insert -- hypotube; --, therefor.

Signed and Sealed this
Second Day of February, 2016

Michelle K. Lee
*Director of the United States Patent and Trademark Office*